(12) United States Patent
Bryce

(10) Patent No.: US 8,630,970 B2
(45) Date of Patent: *Jan. 14, 2014

(54) METHODS AND SYSTEMS FOR GENERATING MEDICAL REPORTS

(76) Inventor: Thomas Bryce, Chestnut Ridge, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/487,919

(22) Filed: Jun. 4, 2012

(65) Prior Publication Data

US 2012/0330876 A1    Dec. 27, 2012

Related U.S. Application Data

(63) Continuation of application No. 12/395,256, filed on Feb. 27, 2009, now Pat. No. 8,195,594.

(60) Provisional application No. 61/032,677, filed on Feb. 29, 2008.

(51) Int. Cl.
G06F 17/00    (2006.01)
G06N 5/02    (2006.01)

(52) U.S. Cl.
USPC .......................................................... 706/47

(58) Field of Classification Search
USPC .......................................................... 706/47
See application file for complete search history.

(56) References Cited

U.S. PATENT DOCUMENTS

| | | | |
|---|---|---|---|
| 8,195,594 B1 * | 6/2012 | Bryce | 706/47 |
| 2006/0241353 A1 | 10/2006 | Makino et al. | |
| 2007/0237377 A1 | 10/2007 | Oosawa | |

FOREIGN PATENT DOCUMENTS

| | | |
|---|---|---|
| EP | 2169577 A1 | 3/2010 |
| WO | 2011036585 A1 | 3/2011 |

OTHER PUBLICATIONS

European Search Report for EP12170720.2 mailed on Jan. 23, 2013.
European Written Opinion for EP12170720.2 mailed on Jan. 23, 2013.

* cited by examiner

*Primary Examiner* — Michael B Holmes
(74) *Attorney, Agent, or Firm* — Schnader Harrison Segal & Lewis LLP

(57) ABSTRACT

Disclosed is a networked database-driven system for facilitating the generation by multiple users of reports containing frequently occurring, repetitive, or predictable elements, through the system making predictions or suggestions regarding elements to insert into or changes to make to a currently edited report in progress by one user, through the use of user-defined report elements and user-defined relations between those elements, as well as the system's drawing upon collected data regarding prior reports and report elements entered into the system by previous report authors and inclusion or exclusion decisions made by previous report authors regarding those elements in relation to other report elements.

23 Claims, 23 Drawing Sheets

FIG. 4

REPORT EDITING SYSTEM

CT Abdomen Pelvis

Phrase groups:

Lung bases

Abdomen

Pelvis

Bones and soft tissues

FINDINGS

The lung bases are clear. No pleural effusions or pulmonary consolidation is evident at the lung bases.
There is a normal appearance of the liver, gallbladder, spleen, pancreas, kidneys, adrenal glands, and bowel.
No free fluid or free air. No significant lymphadenopathy.
The bones and soft tissues appear within normal limits.

IMPRESSION

1. Unremarkable CT examination of the abdomen and pelvis. Normal appearance of the abdominal organs and bowel.
2. No free fluid or free air.

FIG. 5

REPORT EDITING SYSTEM        FINDINGS

CT Abdomen Pelvis

The lung bases are clear. No pleural effusions or pulmonary consolidation is evident at the lung bases.
There is a normal appearance of the liver, gallbladder, spleen, pancreas, kidneys, adrenal glands, and bowel.
No free fluid or free air. No significant lymphadenopathy.
The bones and soft tissues appear within normal limits.

Phrase groups:

Lung bases

Abdomen

Liver
Spleen
Gallbladder

Gallstones without inflammation
Gallbladder sludge
Acute cholecystitis

IMPRESSION

1. Unremarkable CT examination of the abdomen and pelvis. Normal appearance of the abdominal organs and bowel.
2.  No free fluid or free air.

FIG. 6

REPORT EDITING SYSTEM

| CT Abdomen Pelvis |

Phrase groups:

| Lung bases |

| Abdomen |

| Pelvis |

| Bones and soft tissues |

Commonly associated expressions:

No ductal dilatation or stones

Gallstone in CBD with biliary dilation

Ultrasound is recommended for further evaluation.

This could be further evaluationed with ultrasound.

FINDINGS

Gallstones are noted in the gallbladder, which is mildly distended. There is mild gallbladder wall thickening, and small pericholecystic fluid. Findings are suggestive of acute cholecystitis. Clinical correlation recommended.
The lung bases are clear. No pleural effusions or pulmonary consolidation is evident at the lung bases.
There is a normal appearance of the liver, spleen, pancreas, kidneys, adrenal glands, and bowel.
No free air. No significant lymphadenopathy.
The bones and soft tissues appear within normal limits.

IMPRESSION

1. Gallstones noted in the gallbladder, with mild gallbladder wall thickening, gallbladder distention, and pericholecystic fluid, suggestive of acute cholecystitis
2. Otherwise unremarkable CT examination of the abdomen and pelvis. Otherwise normal appearance of the abdominal organs and bowel.
3. No free air.

FIG. 7

REPORT EDITING SYSTEM

CT Abdomen Pelvis

Phrase groups:

Lung bases

Abdomen

Pelvis

Bones and soft tissues

Commonly associated expressions:

No ductal dilatation or stones

Gallstone in CBD with biliary dilation

Ultrasound is recommended for further evaluation.

This could be further evaluationed with ultrasound.

FINDINGS

Gallstones are noted in the gallbladder, which is mildly distended. There is mild gallbladder wall thickening, and small pericholecystic fluid. Findings are suggestive of acute cholecystitis. Clinical correlation recommended. A 5 mm gallstone is also seen in the common bile duct in the pancreatic head, with mild intra and extrahepatic biliary ductal dilatation. The lung bases are clear. No pleural effusions or pulmonary consolidation is evident at the lung bases. There is otherwise a normal appearance of the liver, spleen, pancreas, kidneys, adrenal glands, and bowel. No free air. No significant lymphadenopathy. The bones and soft tissues appear within normal limits.

IMPRESSION

1. Gallstones noted in the gallbladder, with mild gallbladder wall thickening, gallbladder distention, and pericholecystic fluid, suggestive of acute cholecystitis.
2. 5 mm gallstone in the common bile duct with mild biliary tract dilation.
3. Otherwise unremarkable CT examination of the abdomen and pelvis. Otherwise normal appearance of the abdominal organs and bowel.
4. No free air.

FIG. 8

REPORT EDITING SYSTEM

| CT Abdomen Pelvis |

Phrase groups:

| Lung bases |

| Abdomen |

| Pelvis |

| Bones and soft tissues |

Commonly associated expressions:

| No ductal dilatation or stones |

| Gallstone in CBD with biliary dilation |

| Ultrasound is recommended for further evaluation. |

| This could be further evaluationed with ultrasound. |

FINDINGS

Gallstones are noted in the gallbladder, which is mildly distended. There is mild gallbladder wall thickening, and small pericholecystic fluid. Findings are suggestive of acute cholecystitis. Clinical correlation recommended. A 5 mm gallstone is also seen in the common bile duct in the pancreatic head, with mild intra and extrahepatic biliary ductal dilatation. The lung bases are clear. No pleural effusions or pulmonary consolidation is evident at the lung bases. There is mild degenerative disease of the lumbar spine. There is otherwise a normal appearance of the liver, spleen, pancreas, kidneys, adrenal glands, and bowel. No free air. No significant lymphadenopathy. No aggressive appearing bony lesions are seen. The soft tissues appear within normal limits.

IMPRESSION

1. Gallstones noted in the gallbladder, with mild gallbladder wall thickening, gallbladder distention, and pericholecystic fluid, suggestive of acute cholecystitis.

2. 5 mm gallstone in the common bile duct with mild biliary tract dilation.

3. Mild degenerative disease of the lumbar spine.

4. Otherwise unremarkable CT examination of the abdomen and pelvis. Otherwise normal appearance of the abdominal organs and bowel.

5. No free air.

FIG. 9

REPORT EDITING SYSTEM

CT Abdomen Pelvis

Phrase groups:

Lung bases

Abdomen

Pelvis

Bones and soft tissues

Commonly associated expressions:

No ductal dilatation or stones

Gallstone in CBD with biliary dilation

Ultrasound is recommended for further evaluation.

This could be further evaluationed with ultrasound.

FINDINGS

Gallstones are noted in the gallbladder, which is mildly distended. There is mild gallbladder wall thickening, and small pericholecystic fluid. Findings are suggestive of acute cholecystitis. Clinical correlation recommended. A 5 mm gallstone is also seen in the common bile duct in the pancreatic head, with mild intra and extrahepatic biliary ductal dilatation. The lung bases are clear. No pleural effusions or pulmonary consolidation is evident at the lung bases. There is mild degenerative disease of the lumbar spine. There is otherwise a normal appearance of the liver, spleen, pancreas, kidneys, adrenal glands, and bowel. No free air. No significant lymphadenopathy. No aggressive appearing bony lesions are seen. The soft tissues appear within normal limits.

IMPRESSION

1. Gallstones noted in the gallbladder, with mild gallbladder wall thickening, gallbladder distention, and pericholecystic fluid, suggestive of acute cholecystitis.

2. 5 mm gallstone in the common bile duct with mild biliary tract dilation.

3. Mild degenerative disease of the lumbar spine.

4. Otherwise unremarkable CT examination of the abdomen and pelvis. Otherwise normal appearance of the abdominal organs and bowel.

FIG. 10

| Report text being edited: | Search box: | |
|---|---|---|
| | | |

FIG. 11

| Report text being edited: | Search box: | negative abdominal ct |
|---|---|---|
| | | Title: Negative abdominal CT study with contrast<br>Findings: There is a normal appearance of the abdominal<br>organs and bowel. No free fluid or free air. The bones<br>and soft tissues appear unremarkable.<br>Impression: Normal contrasted CT of the abdomen. |
| | | Title: Negative abdominal CT study with contrast<br>Findings: There is a normal appearance of the liver,<br>spleen, gallbladder, kidneys, adrenal glands, pancreas,<br>and bowel. The vascular structures enhance normally.<br>No aggressive appearing bone lesions are seen.<br>Impression: Negative abdominal CT with contrast. |
| | | Title: Negative unenhanced abdominal CT<br>Findings: No abnormality of the abdomen or bowel<br>noted on unenhanced CT examination of the abdomen.<br>Impression: Normal study. |
| | | |

FIG. 12

| Report text being edited: | Search box: | |
|---|---|---|
| Findings:<br>There is a normal appearance of the abdominal organs and bowel.<br><br>No free fluid or free air.<br><br>The bones and soft tissues appear unremarkable.<br><br>Impression:<br>Normal contrasted CT of the abdomen. | Title: Bilateral lung base atelectasis<br>There is bilateral pulmonary opacity noted at the lung bases, which likely represents atelectasis<br><br>Title: Mild degeneration Lspine<br>There is mild degenerative disease of the lumbar spine.<br><br>Title: Minor scoliosis L spine<br>There is minor scoliosis of the lumbar spine, convex to the [LEFT or RIGHT].<br><br>Title: Noncalcified lung base nodule<br>There is a ___ mm noncalcified nodule noted at the [RIGHT or LEFT] lung base, which is nonspecific in appearance.<br><br>Title: Lung base emphysema<br>[MILD or MODERATE or SEVERE] pulmonary emphysema is noted at the lung bases.<br><br>Title: Prostatomegaly<br>There is [MILD or MODERATE or SEVERE] prostatomegaly.<br><br>Title: Vascular calcifications<br>There are diffuse vascular calcifications, consistent with atherosclerotic disease.<br><br>Title: Probable osteopenia<br>There appears to be osteopenia. | |

FIG. 13

| Report text being edited: | Search box: | |
|---|---|---|
| Findings:<br>There is a normal appearance of the abdominal organs and bowel.<br><br>No free fluid or free air.<br><br>The bones and soft tissues appear unremarkable.<br><br>There is no hydronephrosis or hydroureter.<br><br>No radiopaque gallstones are seen.<br><br>The appendix appears normal.<br><br>The abdominal aorta is normal in size.<br><br>Impression:<br>Normal contrasted CT of the abdomen. | Title: Bilateral lung base atelectasis<br>There is bilateral pulmonary opacity noted at the lung bases, which likely represents atelectasis<br><br>Title: Mild degeneration Lspine<br>There is mild degenerative disease of the lumbar spine.<br><br>Title: Minor scoliosis L spine<br>There is minor scoliosis of the lumbar spine, convex to the [LEFT or RIGHT].<br><br>Title: Noncalcified lung base nodule<br>There is a ___ mm noncalcified nodule noted at the [RIGHT or LEFT] lung base, which is nonspecific in appearance.<br><br>Title: Lung base emphysema<br>[MILD or MODERATE or SEVERE] pulmonary emphysema is noted at the lung bases.<br><br>Title: Prostatomegaly<br>There is [MILD or MODERATE or SEVERE] prostatomegaly.<br><br>Title: Vascular calcifications<br>There are diffuse vascular calcifications, consistent with atherosclerotic disease.<br><br>Title: Probable osteopenia<br>There appears to be osteopenia. | |

FIG. 14

| Report text being edited: | Search box: | renal mass hydronephrosis enhances |
|---|---|---|
| Findings:<br>There is a normal appearance of the abdominal organs and bowel.<br><br>No free fluid or free air.<br><br>The bones and soft tissues appear unremarkable.<br><br>There is no hydronephrosis or hydroureter.<br><br>No radiopaque gallstones are seen.<br><br>The appendix appears normal.<br><br>The abdominal aorta is normal in size.<br><br>Impression:<br>Normal contrasted CT of the abdomen. | | Title: Probable renal cell carcinoma with hydro<br>There is an approximately ___ cm mass seen in the [RIGHT or LEFT] kidney, which enhances with contrast.<br>This most likely represents renal cell carcinoma.<br>There is also moderate right sided hydronephrosis.<br><br>Title: Renal cell carcinoma<br>There is an approximately ___ cm mass in the<br>[RIGHT or LEFT] kidney which enhances with contrast and is likely a renal cell carcinoma.<br><br>Title: Renal mass<br>In the [RIGHT or LEFT] kidney, a ___ cm mass is<br>present. This could represent a complex cyst,<br>though renal cell carcinoma is not excluded. |

FIG. 15

| Report text being edited: | Search box: | |
|---|---|---|
| Findings:<br>There is an approximately 5 cm mass seen in the right kidney, which enhances with contrast.<br><br>This most likely represents renal cell carcinoma.<br><br>There is also moderate right sided hydronephrosis.<br><br>There is a normal appearance of the abdominal organs and bowel.<br><br>No free fluid or free air.<br><br>The bones and soft tissues appear unremarkable.<br><br>There is no hydronephrosis or hydroureter.<br><br>No radiopaque gallstones are seen.<br><br>The appendix appears normal.<br><br>The abdominal aorta is normal in size.<br><br>Impression:<br>Normal contrasted CT of the abdomen. | Title: Probable renal cell carcinoma with hydro<br>There is an approximately ___ cm mass seen in the [RIGHT or LEFT] kidney, which enhances with contrast. This most likely represents renal cell carcinoma. There is also [MILD or MODERATE or SEVERE] right sided hydronephrosis.<br><br>> Impression counterpart:<br>___ mass in the [R or L] kidney, likely a RCC, associated with [Mild/Moderate/Severe] [R or L] hydronephrosis<br><br>Title: Renal cell carcinoma<br>There is an approximately ___ cm mass in the<br>[RIGHT or LEFT] kidney which enhances with contrast and is likely a renal cell carcinoma.<br><br>Title: Renal mass<br>In the [RIGHT or LEFT] kidney, a ___ cm mass is present. This could represent a complex cyst, though renal cell carcinoma is not excluded. | |

FIG. 16

| Report text being edited: | Search box: |
|---|---|
| Findings:<br>There is an approximately 5 cm mass seen in the right kidney, which enhances with contrast.<br><br>This most likely represents renal cell carcinoma.<br><br>There is also moderate right sided hydronephrosis.<br><br>*There is a normal appearance of the abdominal organs and bowel.*<br><br>No free fluid or free air. The bones and soft tissues appear unremarkable.<br>*There is no hydronephrosis or hydroureter.*<br><br>No radiopaque gallstones are seen.<br><br>The appendix appears normal.<br><br>The abdominal aorta is normal in size.<br><br>Impression:<br>1) 5 mass in the right kidney, likely a RCC, associated with moderate right hydronephrosis.<br><br>2) *Normal contrasted CT of the abdomen.* | Title: Probable renal cell carcinoma with hydro<br>There is an approximately ___ cm mass seen in the [RIGHT or LEFT] kidney, which enhances with contrast. This most likely represents renal cell carcinoma. There is also [MILD or MODERATE or SEVERE] right sided hydronephrosis.<br><br>> Impression counterpart:<br>___ mass in the [R or L] kidney, likely a RCC, associated with [Mild/Moderate/Severe] [R or L] hydronephrosis<br><br>Title: Renal cell carcinoma<br>There is an approximately ___ cm mass in the [RIGHT or LEFT] kidney which enhances with contrast and is likely a renal cell carcinoma.<br><br>Title: Renal mass<br>In the [RIGHT or LEFT] kidney, a ___ cm mass is present. This could represent a complex cyst, though renal cell carcinoma is not excluded. |

FIG. 17

| Report text being edited: | Search box: | |
|---|---|---|
| Findings:<br>There is an approximately 5 cm mass seen in the right kidney, which enhances with contrast.<br><br>This most likely represents renal cell carcinoma.<br><br>There is also moderate right sided hydronephrosis.<br>*There is a normal appearance of the abdominal organs and bowel.*<br><br>No free fluid or free air.<br><br>The bones and soft tissues appear unremarkable.<br><br>*There is no hydronephrosis or hydroureter.*<br><br>No radiopaque gallstones are seen.<br><br>The appendix appears normal.<br><br>The abdominal aorta is normal in size.<br><br>Impression:<br>1) 5 mass in the right kidney, likely a RCC, associated with moderate right hydronephrosis.<br>2) *Normal contrasted CT of the abdomen.* | There is otherwise a normal appearance of the abdominal organs and bowel.<br><br>No other significant intraabdominal or pelvic pathology is noted. | |

FIG. 18

| Report text being edited: | Search box: | |
|---|---|---|
| Findings:<br>There is an approximately 5 cm mass seen in the right kidney, which enhances with contrast.<br><br>This most likely represents renal cell carcinoma.<br><br>There is also moderate right sided hydronephrosis.<br><br>There is otherwise a normal appearance of the abdominal organ and bowel<br><br>No free fluid or fee air. The bones and soft tissues appear unremarkable.<br><br>No radioplaque gallstones are seen.<br><br>The appendix appears normal.<br><br>The abdominal aorta is normal in size.<br><br>Impression:<br>1) 5 mass in the right kidney, likely a RCC, associated with moderate right hydronephrosis. | | |

FIG. 19

| Report text being edited: | Search box: | |
|---|---|---|
| Findings:<br>There is an approximately 5 cm mass seen in the right kidney, which enhances with contrast. This most likely represents renal cell carcinoma.<br><br>Other possibilities would include a renal angiomyelolipoma with hemorrhage. This could be further evaluated by examination with an unenhanced CT study.<br><br>There is also moderate right sided hydronephrosis. The hydronephrosi may relate to hemorrhage within the urinary tract secondary to the mass. Urinalysis evaluation is recommended.<br><br>There is otherwise a normal appearance of the abdominal organ and bowel.<br><br>No free fluid or fee air.  The bones and soft tissues appear unremarkable.<br><br>No radioplaque gallstones are seen<br><br>The appendix appears normal.<br>The abdominal aorta is normal in size.<br><br>Impression:<br>1) 5 mass in the right kidney, likely a RCC or hemorrhagic AML, associated with moderate right hydronephrosis. | | |

FIG. 20

| Report text being edited: | Search box: | |
|---|---|---|
| Findings:<br>There is an approximately 5 cm mas seen in the right kidney, which enhances with contrast. This most likely represents renal cell carcinom.<br><br>Other possibilities would include a renal angiomyelolipoma with hemorrhage. This could be further evaluated by examination with an unenhanced CT study.<br><br>There is also moderate right sided hydronephrosis. The hydronephrosis may relate to hemorrhage within the urinary tract secondary to the mass Urinalysis evaluation is recommende<br><br>There is otherwise a normal appearance of the abdominal organ and bowel.<br><br>No free fluid or fee air. The bones a soft tissues appear unremarkable.<br><br>No radioplaque gallstones are seen.<br><br>The appendix appears normal.<br><br>The abdominal aorta is normal in siz<br><br>Impression:<br>1) 5 mass in the right kidney, likely RCC or hemorrhagic AML, associate( with moderate right hydronephrosis | Title: Invasive angiomyelolipoma<br>The mass, consistent with an angiomyelolipoma, extends into the right renal vein, IVC, and right atrium.<br><br>Title: Noninvasive angiomyelolipoma<br>The mass does not appear to extend into adjacent vascular structures or invade local soft tissue structures.<br><br>Title: Angiomyelolipoma benign<br>Renal angiomyelolipomas are generally considered to be benign tumors. There are no reported cases of distant metastases, though cases have been reported where there has been extensive local invasion.<br><br>Title: Angiomyelolipoma workup<br>This mass could be further evaluated by a thin section unenhanced CT study, an MR study, or by angiography if findings are inconclusive on cross sectional imaging. | |

FIG. 21

| Report text being edited: | Search box: |
|---|---|
| Findings:<br>There is an approximately 5 cm mas seen in the right kidney, which enhances with contrast. This most likely represents renal cell carcinom. | Title: Invasive angiomyelolipoma<br>The mass, consistent with an angiomyelolipoma, extends into the right renal vein, IVC, and right atrium. |
| Other possibilities would include a renal angiomyelolipoma with hemorrhage. This could be further evaluated by examination with an unenhanced CT study. | Title: Noninvasive angiomyelolipoma<br>The mass does not appear to extend into adjacent vascular structures or invade local soft tissue structures. |
| Renal angiomyelolipomas are gener considered to be benign tumors. There are no reported cases of dista metastases, though cases have beel reported where there has been extensive local invasion. | Title: Angiomyelolipoma benign<br>Renal angiomyelolipomas are generally considered to be benign tumors. There are no reported cases of distant metastases, though cases have been reported where there has been extensive local invasion. |
| There is also moderate right sided hydronephrosis. The hydronephrosis may relate to hemorrhage within th urinary tract secondary to the mass Urinalysis evaluation is recommende | Title: Angiomyelolipoma workup<br>This mass could be further evaluated by a thin section unenhanced CT study, an MR study, or by angiography if findings are inconclusive on cross sectional imaging. |
| There is otherwise a normal appearance of the abdominal organ and bowel. | |
| No free fluid or fee air. The bones a soft tissues appear unremarkable. | |
| No radioplaque gallstones are seen. | |
| The appendix appears normal.<br>The abdominal aorta is normal in siz | |
| Impression:<br>1) 5 mass in the right kidney, likely RCC or hemorrhagic AML, associatec with moderate right hydronephrosis | |
| 2) This mass could be further evaluated by a thin section unenhanced CT study, an MR study, by angiography if findings are inconclusive on cross sectional imaging. | |

FIG. 23

METHODS AND SYSTEMS FOR GENERATING MEDICAL REPORTS

This application is a continuation of U.S. patent application Ser. No. 12/395,256, filed Feb. 27, 2009, entitled Methods and Systems for Generating Medical Reports, which in turn is based on, and claims priority to, U.S. provisional application Ser. No. 61/032,677, filed Feb. 29, 2008, entitled Report Generation Methods and Systems.

BACKGROUND OF THE INVENTION

In medical diagnostic imaging, interpreters of examinations generate free-flowing text reports regarding the presence or absence of imaging findings on examinations which they interpret, and their determinations regarding the diagnostic significance of such findings. Great efforts are expended by individual study interpreters to produce reports which contain commonly recurring phrases, structures, and concepts. The mental labor and time involved in generating such reports is a major productivity-limiting factor.

To date, this problem has been addressed in a limited fashion through the use of pre-fabricated phrases and report templates. Pre-fabricated phrases are lists of commonly used expressions, which report authors can draw upon when generating a report, by inserting relevant phrases into the report text, stringing such pre-defined expressions together, and entering additional free-form text, to form a final report. Templates are prefabricated frameworks for complete reports regarding commonly encountered findings, with certain pieces of information left blank, which the report author fills in at the time of final report preparation.

Generating reports through the use of pre-defined expressions remains laborious as the mental work involved in choosing appropriate expressions, organizing the expressions, and in excluding or modifying incompatible expressions, for the report, remains entirely the task of the report author. In fact, a report author may have to devote additional time to ensure that prefabricated phrases which were inserted into the report do not include any features inconsistent with one another.

Another limitation of systems of pre-written phrases is that only commonly used phrases which would interest a "critical mass" of users of the pre-written phrase system are available to report authors. Such "copy-and-paste" pre-written expression systems do not adequately address the needs of users writing reports regarding unusual circumstances which may be encountered repeatedly, but with insufficient frequency to make it worth including suitable phrases into the standard "lexicon" of pre-set phrases. Placing too many such infrequently used phrases into the standard distributed set of phrases would cause the phrase set to be large, unwieldy, and difficult to navigate.

When templates are used, it is necessary for the report author to devote considerable effort to the task of modifying templates to fit the unique circumstances of the case being reported. A particular limitation of template-based systems used in existing report generation technologies is that such systems are highly structured and rigidly defined. Such systems consist of rigidly formed blocks of text with blank areas for the author to fill in by voice recognition, typing, or other means. This technology does not offer sufficient flexibility for use in reporting cases which deviate from a limited set of pre-determined patterns.

Accordingly, there is a need for report authors to employ a "smart" report generation method to generate reports in a more time-efficient manner. There is also a need to allow report authors to have a mechanism to reduce likelihood of errors or oversights in reporting.

SUMMARY OF THE INVENTION

Embodiments of the invention can provide a consistent and time-efficient method for radiologists and other medical image study interpreters to report both normal and abnormal medical findings using frequently repeated phrases. The inventor has uniquely recognized that commonly used phrases in radiology reports do not exist in isolation, but rather in predictable, inter-related patterns, and has used this to create a novel report generation tool. Still further, by recognizing that predictable, inter-related patterns exist, the inventor's system deviates from traditional views that report generation could not be automated to this level. The inventor has additionally recognized that phrases extracted from the text of reports generated by previous users, as well as decisions made by previous users regarding the insertion or deletion of phrases from reports, are data which can be drawn upon to generate suggestions regarding report content for future report authors.

The report generation method exploits the existence of relationships between commonly used medical phrases to aid in navigating the available phrases, with such relationships at first defined explicitly by the user(s), with additional phrases subsequently extracted by the system through data collected through the experience of prior users regarding useful phrases, to enable users to generate reports using these useful, interrelated medical phrases in a more time efficient manner.

Such a system would also address the need for a mechanism to reduce likelihood of errors in reporting, such as failures to report essential information in given medical contexts.

The invention deviates from existing report generation tools that do not exploit the presence of relationships between the phrases, and which also do not draw upon data collected in the course of the use of the system by previous report authors, and therefore cannot be automated to the level of the current invention.

The invention seeks to facilitate the generation of medical imaging study reports by exploiting patterns of repetitive themes and networked ideas to speed up report generation. These patterns exist in the logic of medical reports and can be used to speed up and to simplify the process of generating medical reports. These patterns may include, for example certain commonly expressed medical ideas which are associated with or suggest other commonly expressed medical ideas, or certain commonly expressed medical ideas that exclude other commonly expressed medical ideas, or the fact that addressing certain topics in such reports often suggests repeatedly utilized lists of additional topics that need to be addressed. Such inclusion patterns, also known as inclusion rules, are applied to the phrases selected by the report author to provide suggestions regarding additional phrases which the author may wish to insert into the report in progress. Similarly, the exclusion patterns, also known as exclusion rules, are applied to the selected phrases and relevant phrases to eliminate phrases that are contradictory to each other to ensure consistency in the reported findings.

The phrases used in the system initially are defined explicitly by the user, and relationships between phrases (phrases which relate to one another through inclusion or exclusion rules, or "potential alternative" rules, described below), are initially explicitly defined by the user. For example, a user may define several phrases, then indicate that when a certain phrase is inserted into the report, certain other phrases should be flagged as potentially useful, for consideration for insertion into the report. Alternatively, a user may specify that certain phrases are incompatible, and that when one phrase is inserted into the report, certain other phrases (if present) should be removed. These relationships involve "suggested additional" phrases and "excluded" phrases.

An additional type of relationship that may be specified includes "potential alternative" phrases. When a given phrase is excluded from a report due to incompatibility with another phrase, "potential alternative" phrases may be automatically inserted in place of the excluded phrase, if the potential alternative phrase remains compatible with the other phrases in the report.

The inventor has recognized that as such a report system is used over time by multiple users, who use the system to craft complete medical imaging reports, the text of previous reports entered into the system, as well as information regarding the insertion and deletion of specific phrases performed by previous users in the course of writing reports, provides a valuable set of information regarding potentially useful phrases, and their relationship with one another, which may be used to offer suggestions to future users as they write reports. This is due to the fact that diagnostic imaging related reports are made regarding particular body parts and particular imaging modalities, with a range of predictable pathologic or normal findings, and such reports tend to be highly repetitive and involve a large number of frequently re-used elements. Thus, the inventor's report generation system not only allows users to define useful phrases and relationships between those phrases, but also actively seeks to define and suggest further potentially useful phrases by examining the patterns of usage of the system by other report authors for relevance to the current author's report in progress.

The system may, for example, identify potentially useful text from a previously written report due to the presence of unusual words in that previously generated text, which matches unusual words in a current author's report in progress. If that author selects the text in question and inserts it into the report in progress, the system is informed that the text, or "phrase," is indeed potentially useful. The system then stores information such as various characteristics regarding that phrase, as well as other actions taken by the user in the same report into which the phrase was inserted, such as the insertion of other phrases (which may become "suggested additional" phrases), and the removal of other phrases (which may acquire an "excluded" relationship with the originally inserted phrase). As a "phrase" generated in such an automatic manner is repeatedly used, and as usage patterns regarding such phrases emerge, such as the common insertion of certain other phrases along with the phrase in question, the system develops a database of information regarding such phrases and their relationships with other phrases that may be used to improve the capacity of the system to offer useful suggestions to users as they write reports.

In one implementation of the invention, the user defines sets of phrases that are useful for particular anatomical regions of interest, allowing the user to limit the full set of possible phrases to suggest only those phrases most relevant to the medical imaging study at hand. Based on the selection of study type data based on anatomical regions, relevant phrases or templates are presented to the report authors for consideration for insertion into the text fields.

The suggested set of phrases may also be influenced by other medical imaging study related "meta-data" which are stored along with the actual images in most medical imaging data formats, such as the almost universally used Digital Imaging and Communications in Medicine (DICOM) format.

Such meta-data includes information the type of imaging modality that was performed, and regarding which anatomic regions were imaged, as well as other potentially relevant information such as patient age and sex.

A further embodiment of the invention is directed to systems for generating medical imaging study reports that include one or more input devices configured to input medical imaging study data and user selection of study type, phrase selection and other graphics or text; one or more processors configured to process medical imaging study data, study type selection, and phrase selection; one or more memory systems coupled to the one or more processors configured to store a medical report file containing one or more templates, study type data, phrase data and a plurality of text fields to generate a medical imaging study report; one or more processors configured to process the medical imaging study data to influence which phrases are presented to the user as most potentially useful; one or more memory systems coupled to the one or more processors configured to store user-selected study type data and relevant phrases data; one or more processors configured to process one or more inclusion rules relating to phrases; one or more processors configured to process exclusion rules relating to phrases to omit contradictory phrases from presentation to the user; and an output device connected to the processor configured to display the generated medical report.

DESCRIPTION OF THE DRAWINGS

FIGS. 3-21 are diagrams illustrating the computer interface at various stages of generating a medical imaging data report according to an illustrative embodiment of the invention.

FIGS. 22-23 are screen shots of the system interface according to an illustrative embodiment of the invention.

DETAILED DESCRIPTION OF THE INVENTION

Figure 1:
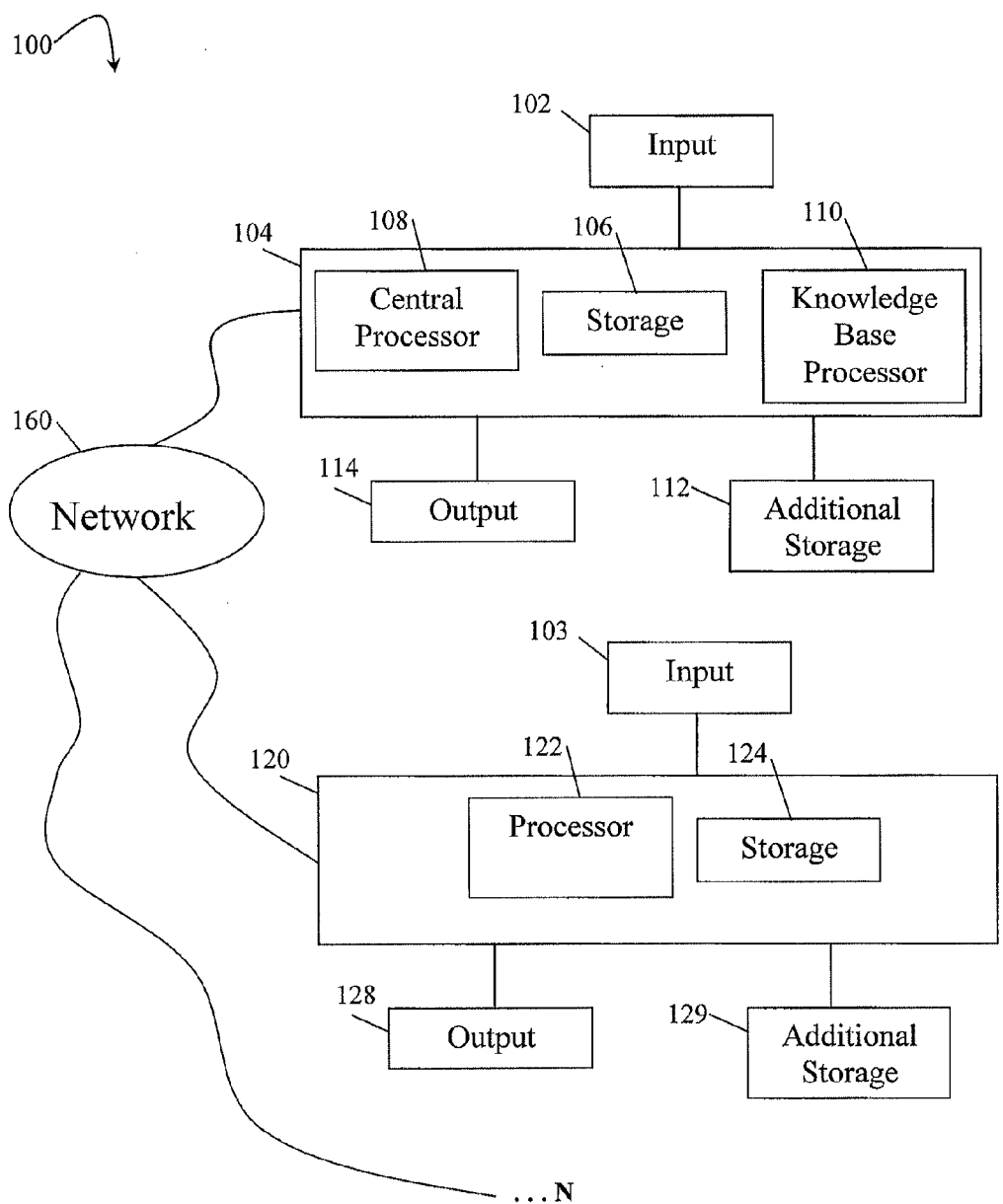
FIG. 1 is a diagram of the computer system according to an illustrative embodiment of the invention.

Following is a description of methods and systems for creating and generating medical imaging study reports according to illustrative embodiments of the invention.

Methods and systems described herein allow a user to quickly formulate and generate medical imaging study reports. Elements of the system include the option to select a study type corresponding to the anatomical region to be studied, which may limit or influence the phrases presented for consideration, a report framework, consisting of a set of text fields corresponding to commonly utilized components into which reports are commonly organized (such as "Findings" and "Impressions" sections), and into which fields the actual report text will be entered, a set of "phrases", or text expressions which may be useful for insertion into reports, relationships defined between such phrases (such as certain phrases which suggest the inclusion or exclusion of certain other phrases), as well as "templates."

The term "template" is used in prior work to denote a pre-fabricated relatively complete report, which involves blank fields to be filled in by the report author, to generate a complete report. The current invention offers a means of beginning the process of report editing with a relatively complete report, thus the term "template" is again employed in the present context to describe a similar idea. However, in the case of this invention, such "templates" do not comprise merely a rigid text framework which must be modified manually in detail to suit the particulars of the unique cases for whose report the template has been applied, but rather, in this invention, "templates" consist of a set of phrases used sequentially to generate a stream of report text. The crucial difference between this invention's implementation of templates and "templates" utilized in prior work is that each phrase in the report retains its unique identify as a phrase, and retains relationships with other phrases both within the report as well as within the phrase database of the invention. This means that as the template is customized into a final report for a particular case, for example, through the insertion of additional phrases into the report framework that was initially populated with text by the template, processing of the report text will be affected by relationships between the template phrases and other phrases. For example, a newly inserted phrase may be incompatible with a phrase used in the template; when such a phrase is inserted, the phrase with which it is incompatible may be automatically removed from the report, or flagged for consideration for removal. Likewise, the patterns of phrases suggested for consideration for inclusion in the report will similarly be influenced by the total set of phrases contained within the report, whether due to inclusion in the original template, or later insertion by the user.

Phrases can involve a verbose or long form for insertion into the standard "Findings" section of imaging reports, which contain detailed descriptions of imaging findings and a full discussion of their significance, as well as a short form for inclusion in the standard "Impressions" section of imaging reports, which gives a brief summary of the major conclusions of the examination interpreter.

The knowledge database of the system contains phrases as well as rules or information regarding relationships between phrases (see Illustrative Example 1 below). The system selects phrases from the knowledge database, based on factors including patterns defining relationships among the phrases, for suggestion to the user, who may select such phrases for input to the report in progress. Upon selection of phrases to be inserted into the report architecture, additional phrases are then selected by the processor from the knowledge database to be suggested to the user. This reduces the likelihood that the user will overlook the reporting of details or information that are commonly considered relevant in the context of other information being discussed by the user in the report. Exclusion rules based on incompatibilities between phrases in the knowledge database are applied to the selected phrases to eliminate and/or identify phrases which are incompatible with other included phrases, reducing the likelihood of errors involving reporting contradictory findings. The processor tracks usage patterns (the decisions regarding including and excluding phrases made by the user in the course of report editing), and uploads such patterns to the knowledge database.

FIG. 1 depicts a report generation system 100 according to an illustrative embodiment of the invention. This schematic demonstrates a basic configuration of a system 100, wherein a central server or cluster of servers manages multiple concurrent users of the report editing system via a network 160, accessing a database of templates, phrases, and data regarding phrase and template selection patterns to dynamically organize and make suggestions regarding report content for multiple users. The database, over time, may also include phrases extracted from previously written reports and observed relationships between such phrases.

System 100 generally comprises a central computer 104, such as a server or server complex and one or more (N) local computers 120 connected over a network 160. Local computers 120 may be for example, workstations, image viewing stations, or individual computers. Central computer 104 processes and stores files of medical imaging study reports. Accordingly, central computer 104 includes at least one processor 108 and at least one knowledge database processor 110. Designated processors may be separate or a single processor having a plurality of functions. The knowledge database processor 110 processes medical imaging data from the input 102 and data regarding phrases and relationships between phrases, to generate phrases to be presented to the user via an output 114 for selection to be inserted in the report.

One or more input devices 102 input data and information into central computer 104. The input devices for computer-based, textual, or audio format may include for example a keyboard, touch screen, or dicta-phone. Input devices 102 import data such as medical imaging data and various concepts and phrases data to be selected and modified.

Central computer 104 is also functionally connected to one or more output devices 114. Output devices 114 may include for example, a display, projection, printer, speaker, diskette, or other media for storing and displaying a file of the generated report in various formats. Output devices 114 allow a user to view a finished report or any work-in-progress modification at any stage of the creative process for evaluation. It can also provide a report in various file formats stored on separate storage devices such as DVDs, USB storage devices, or memory cards.

Central computer 104 is depicted as having a storage component 106, however, one or more additional storage devices 112 may also be functionally connected to central computer 104. Such storage may include for example, random access memory (RAM) and read only memory (ROM) devices, CD-ROMs, flash memory, and various other storage disks. Other memory components may also be incorporated into the system to carry out the function of the computers.

Local computers 120 can be employed by users who are generating, reviewing, and modifying phrases and concepts for a report contained in the report file on central computer 104. Therefore, local computers 120 are depicted as having a processor 122 and storage 124. In a particular embodiment of the invention, the application of patterns to various phrases and report generation is performed and saved in the central computer 104, and only the phrases and concepts are selected and modified at the local computers 120. In another embodiment, the phrase and concept selection and application of patterns to various phrases and concepts are performed on the local computers 120. As with the central computer 104, the local computers 120 will have one or more input devices 103, one or more output devices 128, and may also have additional storage 129, illustrative types, which are described above.

Figure 22:
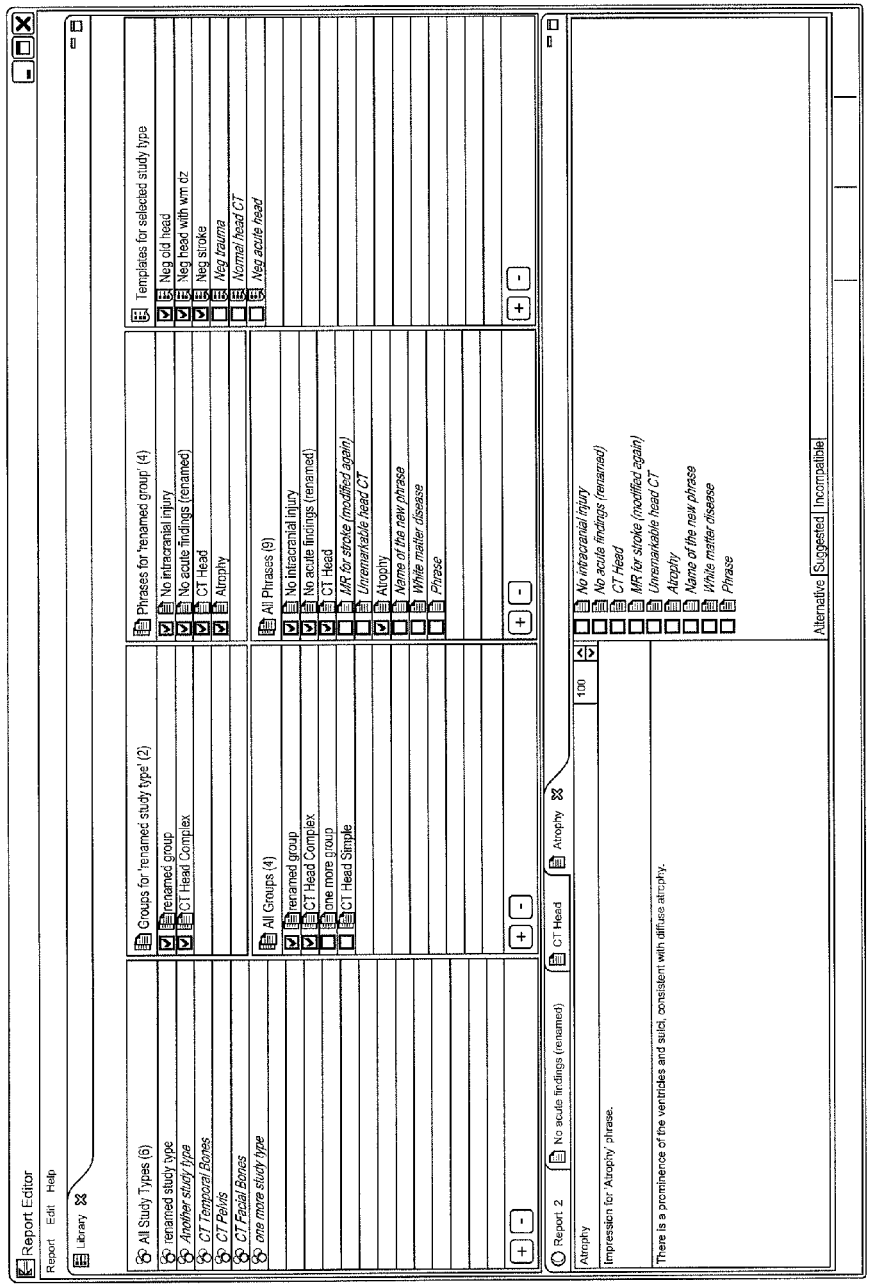

Both the central computer 104 and local computers 120 may include a graphical user interface, for manipulating and displaying suggested and selected phrases in the report file, as shown in FIG. 22.

Each computer described herein may stand alone to receive input data, to process data, to communicate with other computers or processors in the network and to allow users to view various data.

Embodiments of the present invention may also be used with other computer systems such as a network of multiple processors and one or more storage units or a computer with a single processor and one or more storage units.

In the illustrative embodiment as shown in FIG. 1, the central computer 104 and local computer 120 may be embodied in one computer system or may be connected over a network 160 in a variety of configuration such as in parallel, in series or in a hub-and-spoke configuration. The computer network may include, for example, a local area network (LAN), a corporate network or an internetwork such as the Internet. In this illustrative embodiment, the computers are connected via a LAN such as an intranet within an organization. The network allows multiple users to work simultaneously on the multiple sets of medical imaging data within an organization. It may also be set up via the internet to allow multiple parties to input, to view, or to generate medical imaging study reports.

Both the central computer 104 and the local computers 120 may be central processing units (CPU), other centralized or main processors, graphics processing units (GPU), a set of computer-executable instructions, software applications for processing or one or more software applications for processing data relating to the generation of medical imaging study report, including any combination of the aforementioned processors.

It is noted that input imaging data may include but are not limited to data representing images generated by imaging technologies, such as ultrasound, computed tomography (CT), Computer Assisted Tomography (CAT), nuclear medicine, Positron Emission Tomography (PET) and magnetic resonance imaging (MRI). Images can also be captured from a modality such as for example an MRI scanner to a workstation over a network such as the Internet, local area network (LAN), wide area network (WAN) or other networks.

It is further noted that data entry into the system can be by any suitable method, including, but not limited to, keyboard, touch screen or voice.

Figure 2:
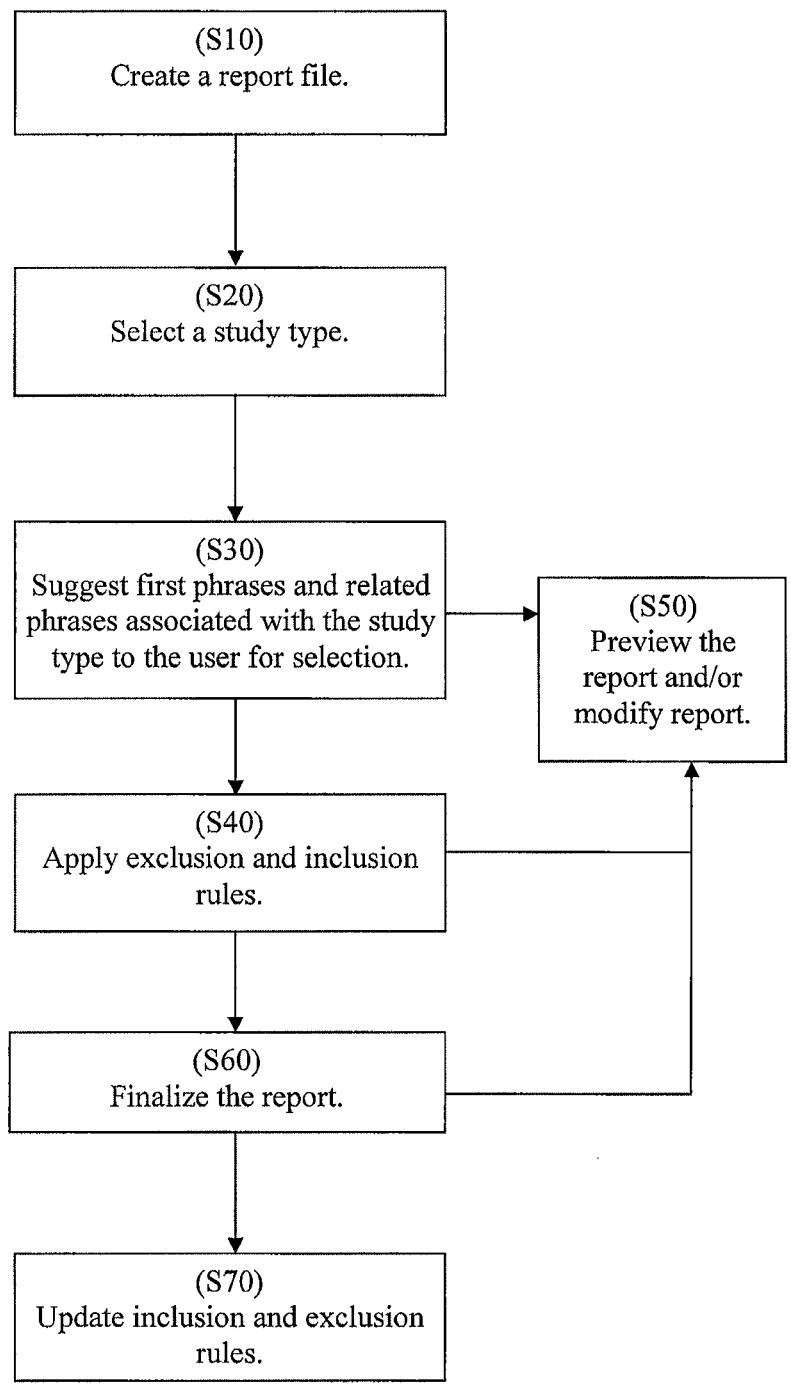
FIG. 2 is a flowchart of a method of according to an illustrative embodiment of the invention.

FIG. 2 is a flowchart for generating a medical imaging study report according to an illustrative embodiment of the invention. A report file is first created on the central computer (S10) or locally and then saved to the central computer. Medical imaging data can be read into the report file or can be a separate file. The report file has an adaptive architecture that includes a study type associated with an anatomical region to be studied and one or more fields or templates to house imaging study interpretation and diagnostic findings. The contents of the report file will be described in more detail below. Since there may be more than one area of interest corresponding to a given anatomical region, one or more study types depicting such areas of interest can be presented to the user via the output device for selection to be a topic of the report. (S20). A user then determines what study type is to be reported. The selected study type is then inputted into the report file. The study type is analogous to the topic of a report. For each study type, one or more diagnostic findings that are typically associated with a given study type are generated by applying rule-based concepts such as inclusion rules at the knowledge database in the central server. Additionally, more phrases are suggested to the user as related phrases or templates at the output device (S30). Rules and patterns in the knowledge database will be described in more detail below. Upon a user's selection being inputted via the input device, the selected phrases are further processed at the server by applying exclusion rules from the knowledge database to exclude contradictory or inconsistent phrases as excluded phrases. Substitution rules may replace the excluded phrases with alternative phrases (S40). If one selected phrase representing one medical finding or concept is inconsistent with other selected phrases or concepts, a user will be alerted to such an inconsistency at the output device or the system can delete an inconsistent phrase. In a particular embodiment of the invention, such phrases may be presented in a designated text field in the report framework for the user to view the potential incompatibility with the remaining selected and/or suggested phrases. This provides the user a safety measure to reduce errors in reporting. A preview of the report in its current stage is available continuously during the report creation and modification process (S50). The steps can be repeated if it is desirable to revise the report or to add additional findings and impressions to the report. Once all selections and modifications are completed, the report is finalized and generated via the output device (S60). A user's pattern of selecting or excluding phrases may be repetitive, and can be generalized as new rules to be uploaded to the knowledge database for future use by multiple users (S70) or can update a knowledge database specific to that user. A more detailed description of aspects of the report generation according to illustrative embodiments of the invention, follow.

Medical imaging study reports are particularly suited to this type of reporting system given that for virtually any type of study, there are a few major systems, organs, and concepts involved, and these body systems, organs, regions, and concepts almost always have a "normal" form and certain limited defined types of "abnormal" findings. Further, the abnormal findings do not exist in isolation, whereby each normal and each abnormal finding has an equal chance of existing in any given report; rather, certain abnormal findings exclude the presence of certain normal findings; and certain abnormal findings suggest that other, related, abnormal findings may also be present.

Various embodiments of this invention exploit the fact that medical imaging study reports, far from being wide-ranging open-ended reports, involve for the most part, a limited set of certain inter-related concepts, which may either suggest or exclude the possibility of the inclusion of other concepts in the report, in order to produce a system that recognizes the presence of such relationships, and uses them to organize the report for the user as the user inserts new ideas into the report being generated. The concept of links existing between commonly used phrases allows the user to define new phrases, and define how such phrases relate to other phrases in the system, and by so doing, customize a "knowledge base" of the system regarding phrases used in report generation. This allows the system to utilize and exploit these relationships to minimize the effort required to generate new reports for new cases.

The knowledge database includes a library of commonly used medical phrases and data regarding how the phrases relate to one another. Additionally, templates can be created that consist of a set of phrases associated with commonly reported situations, such as a standard normal examination of a certain type. Templates as well as phrases may also include blank fields into which a user can enter original text or text selected from a list of possibilities such as a list of adjectives of degree, such as slight vs. mild vs. moderate vs. severe.

The rapid generation of well-structured, thorough radiology reports can be facilitated by recognizing and exploiting the fact that commonly used phrases in radiology reports do not exist in isolation, but rather in predictable, inter-related patterns, wherein the use of one phrase may suggest the need to also insert one or more related phrases, or which may suggest that the use of one phrase may cause others to be excluded.

Each related phrase to be suggested can be associated with a priority value, defined and entered by the user, or determined by the system on the basis of patterns of placement of the phrase within reports by previous users. Such a value is assigned according to the importance of the phrase, with for example, higher values indicating more important information which should be presented first in the report, prior to less important information. For example a phrase referencing a life threatening condition would be associated with a high priority value, and would automatically be inserted toward the beginning of the text of the report in progress, even if this is the last item added to the report, following the addition of less important findings. The user could manually override this priority value-based placement, if desired. Conventional systems require the user to organize the report manually. Accordingly, the priority value feature of the invention can save report authors significant time and effort.

In another aspect of an illustrative embodiment of the invention, users have the ability to define "variables" such as dates or measurements in expressions that they can insert in sub-text fields. That is, they could submit an expression saying "There is a [#] cm mass noted in the right colon which likely represents colon carcinoma. This [#] cm mass extends to and possibly invades the ventral abdominal wall." When the user updates a single instance of this measurement, it will be propagated in both locations in the text edit field on the user's screen, when the template is inserted. Likewise, when the system extracts sentences from the user's current text edit field for insertion into the database as a possible text suggestion, the system could replace dates, measurements, and other situation-specific data with variables that can be set to the specific values required for other instances of use by future users of the text expressions.

Embodiments of this invention can maintain a database of many or all phrases previously used in reports or inserted into standard templates by all users of the system. The illustrative embodiment of the system can incorporate the concept of "standard templates" by allowing users to define a set of templates for their own use, which will also become part of the general database to be used by, or improved upon by, other users. Additionally, text in reports generated through the use of this system can be saved back to the database to continuously improve the suggestions made to users when writing reports. In an exemplary embodiment of the invention, all text in all reports is saved back to the database. The knowledge or report generation database is drawn upon by the system as a means of suggesting report modifications to users working on a report in progress based on use frequency of use of certain phrases of prior users, and based on patterns of usage in which the insertion of certain phrases suggests a high probability that other phrases will be used, or alternatively, wherein the insertion of certain phrases into the body of text is often accompanied by the deletion of other phrases.

The system over time will become self-improving. Users who find an expression or template generated by another user which is suitable for their needs, but requires modifications or improvements, are free to make such modifications or improvements to the template, which will then be again generally available to all or selected users. If the modified phrase or template is subsequently commonly selected for use by other users, more frequently than the original version, prior to the modifications, the new modified version of the phrase or template will be favored by this factor, and this will cause the modified phrase or template to be more commonly presented to future users of the system.

In drawing upon all text in all reports generated by prior users (or designated text in designated reports), the system can generalize and depersonalize the text in prior actual reports, deleting names and identification numbers, and generalizing specific measurements, indications of laterality, indications of severity, and so on. For example, measurements such as "5 cm" can be changed to "[#] cm," with the specific measurement number replaced by a blank. Likewise, a phrase such as "moderate" could be replaced by a set of choices from which the user can insert "mild," "moderate," or "severe" into that report location.

Figure 23:
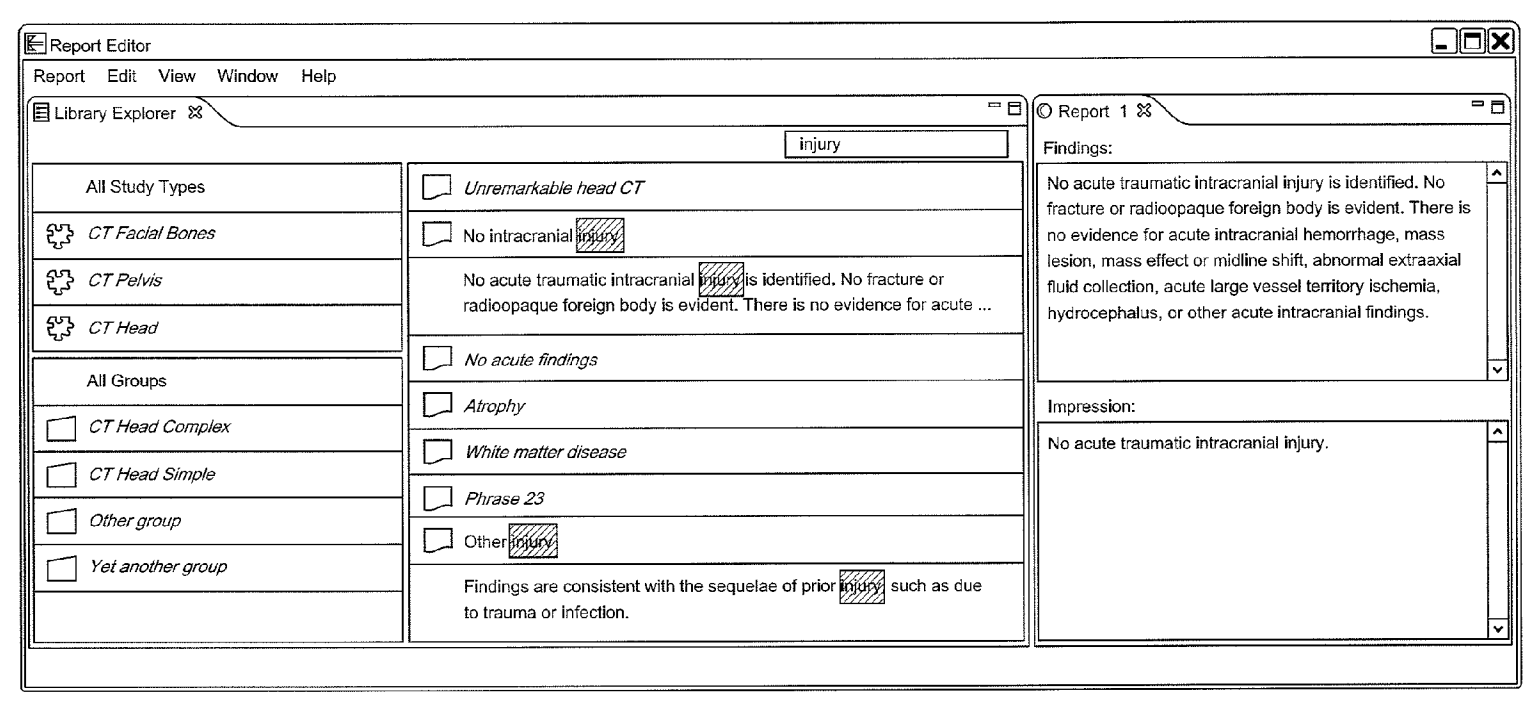

Users can call up report phrase suggestions using a search box as shown in FIG. 23, in which they type a few words which relate to what they wish to report, which would cause the database to be searched for snippets of text or pre-set phrases previously generated by users in the past containing such words. For example, in FIG. 23, by searching the word "injury," previously generated phrases are presented to the user. The text suggestions called up by this search could be sorted according to predicted usefulness, which could be based on factors such as the frequency with which other users have selected the text suggestions in question, the frequency with which other users have selected other text suggestions authored by the same author as a given text suggestion, the frequency with which the current user of the system has selected other text expressions authored by the author of the text suggestion in question, the number of words in the current text edit field being worked on by the current user of the system which also appears in the text suggestion in question, with this last factor amplified by the infrequency of the words in question (infrequently used words which are also present in the user's current report text, which also appear in a possible text suggestion, will increase the probability of the text suggestion being displayed and cause it to be displayed more prominently), medical imaging study meta-data such as patient age and sex, and other such factors.

The system over time would develop phrases applicable to even unusual circumstances, and will begin to incorporate a form of knowledge of the topic for use by future users. Thus, the system could become a knowledge database, in addition to a mere phrase suggestion engine. Though inaccurate information could enter the system, because the presentation of suggestions will be influenced by the frequency with which users accept or reject certain expressions, accurate information or appealing means of expressing concepts would be favored over time as the system is employed by a group of users, and the system benefits from user decisions based on their aggregate knowledge. For example, in the case of diagnostic imaging report generation, lists of possible diagnoses for certain findings will find their way into the system, such as "There is an approximately [#] cm nodule in the [LEFT versus RIGHT] adrenal gland. Hounsfield measurements are [#] HU. Given the low Hounsfield units measurements, this likely represents either an adenoma or a myelolipoma. MRI with in and out of phase imaging would evaluate further."

The means by which the system will suggest phrase insertions or deletions bears a more detailed description.

The system can exploit the patterns of usage of expressions seen over time, in terms of expressions that are commonly selected following the use of other expressions, or expressions that are commonly excluded from report bodies following the use of other expressions, or expressions that are commonly selected based on, for example, the type of study, age of patient, other text currently existing in the report text, to intelligently suggest other possible inclusions to the report text, or possible exclusions from the report text.

That is, if it is observed that a given expression, which we will call expression #2, is commonly inserted into text bodies after expression #1 is inserted, the system shall present a list of suggestions to the user, including expression #2, that they may consider inserting into the report.

Additionally, the system may note that expression #3, if present in the report, is usually removed after expression #1 is inserted. The system may under these circumstances suggest that the user remove expression #3 from the system.

Also, any information available to the system which may impact expression suitability can be exploited for the purpose of making appropriate suggestions. For example, the other text currently in the user's report body can be searched for words, particularly infrequent words, and these can be compared to words in the expressions available to favor their suggestion. For example, if a radiologist is writing a report regarding an unusual type of tumor, other expressions, and things that have been said by other radiologist users of the systems about such tumor types can be shown as suggestions.

Three illustrative examples are presented below to demonstrate the steps involved in generating a medical imaging study report. Illustrative Example 1 describes the data structures (elements of the knowledge base such as phrases and associated rules) which are used in the subsequent two examples.

Illustrative Example 1

The system has the following data structures: (1) study types, (2) phrases and (3) groups. Each study type has the following characteristics: (i) name of study type; (ii) groups of phrases associated with study type; and (iii) the ID# of phrases strung together to make standard normal report. Each phrase has the following characteristics: (i) a phrase ID#, which is not visible to end-user, but is useful for programming; (ii) a title or name for referring to the phrase in menus for the user to recognize; (iii) a priority value, which shows the relative importance of a finding if it is present in the report; (iv) an exclusion list, which contains other phrases that should be eliminated from the report if this phrase is inserted; (v) a suggestion list, which contains other phrases the user may want to insert if this phrase is inserted into a report, and alternate phrases that the system will try to substitute for this phrase, if this phrase is excluded. Each group is a plurality of phrases that have the elements: name of group and ID#s of phrases in the group.

The followings definitions of structures are used:
Study Type Definition
CT Abdomen Pelvis
   Phrase Groups Associated with CT Abdomen Pelvis:
   Lung bases, Abdomen, Pelvis, Bones and Soft tissues
   Standard Normal Report for CT Abdomen Pelvis:
   Insert phrases: 1, 2, 4, 8
Phrase Group Definitions:
   Lung Bases
   Includes phrase: 1
   Abdomen
   Includes phrases: 2, 3, 4, 5, 6, 7, 10, 11, 12
   Pelvis
   Includes phrases: (None used in this example)
   Bones and Soft Tissues
   Includes phrases: 8, 9, 13

PHRASES DEFINITIONS

1) Main Report Body Phrase:
The lung bases are clear. No pleural effusions or pulmonary consolidation is evident at the lung bases.
Title for menus: Lung bases normal
Impression counterpart:
Normal appearance of the lung bases.
Priority value: 1
Excludes: None
Suggests: None
If excluded, attempt to insert: None
Include in groups: Abdomen
2) Main Report Body Phrase:
There is a normal appearance of the liver, gallbladder, spleen, pancreas, kidneys, adrenal glands, and bowel.
Title for menus: Normal abdomen organs and bowel.
Impression counterpart: Same as full phrase
Priority value: 1
Excludes: None
Suggests: None
If excluded, attempt to insert: 3, then ( . . . list of other possibilities)
3) Main Report Body Phrase:
There is a normal appearance of the liver, spleen, pancreas, kidneys, adrenal glands, and bowel.
Title for menus: Normal abd. organs/bowel except gallbladder
Impression counterpart: Same as main phrase
4) Main Report Body Phrase:
No free fluid or free air.
Title for menus: Same as main phrase
Impression counterpart: Same as main phrase
Priority value: 1
Excludes: None
Suggests: None
If excluded, attempt to insert: 5, then 6 if 5 is not possible
5) Main Report Body Phrase:
No free fluid.
Title for menus: Same as main phrase
Impression counterpart: Same as main phrase
Priority value: 1
Excludes: None
Suggests: None
If excluded, attempt to insert: None
6) Main Report Body Phrase:
No free air.
Title for menus: Same as main phrase
Impression counterpart: Same as main phrase
Priority value: 1
Excludes: None
Suggests: None
If excluded, attempt to insert: None
7) Main Report Body Phrase:
No significant lymphadenopathy.
Impression counterpart: Same as main phrase
Priority value: 1
Excludes: None
Suggests: None
If excluded, attempt to insert: None
8) Main Report Body Phrase:
The bones and soft tissues appear within normal limits.
Title for menus: Normal bones & soft tissues
Impression counterpart: Same as main phrase
Priority value: 1
Excludes: None
Suggests: None
If excluded, attempt to insert: 9, ( . . . then list of other possibilities)
9) Main Report Body Phrase:
No aggressive appearing bony lesions are seen. The soft tissues appear within normal limits.
Title for menus: No aggressive bone lesions; normal soft tissues:
Impression counterpart: Same as main phrase
Priority value: 5
Excludes: None
Suggests: None
If excluded, attempt to insert: None
10) Main Report Body Phrase:
Gallstones are noted in the gallbladder, which is mildly distended. There is mild gallbladder wall thickening, and small pericholecystic fluid. Findings are suggestive of acute cholecystitis. Clinical correlation recommended.

Title for menus: Acute cholecystitis
Impression counterpart: Gallstones noted in the gallbladder, with mild gallbladder wall thickening, gallbladder distention, and pericholecystic fluid, suggestive of acute cholecystitis.
Priority value: 70
Excludes: 2, 4, 5, ( . . . and others)
Suggests: 11, 12
If excluded, attempt to insert: None
11) Main Report Body Phrase:
No biliary ductal dilatation is seen. No common bile duct stones are seen.
Title for menus: No biliary dilation or stones Impression counterpart:
No biliary ductal dilatation or common bile duct stones.
Priority value: 5
Excludes: None
Suggests: None
If excluded, attempt to insert: None
12) Main Report Body Phrase:
A [#] mm gallstone is also seen in the common bile duct in the pancreatic head, with [MILD/MODERATE/SEVERE] intra and extrahepatic biliary ductal dilatation.
Title for menu: Gallstone in CBD with biliary dilation
Impression counterpart:
[#] mm gallstone in the common bile duct in the pancreatic head, with [MILD/MODERATE/SEVERE] intra and extrahepatic biliary ductal dilatation.
Priority value: 5
Excludes: None
Suggests: None
If excluded, attempt to insert: None
13) Main Report Body Phrase:
There is mild degenerative disease of the lumbar spine.
Mild degenerative disease of the lumbar spine.
Title for menus: Mild degenerative dz lumbar spine
Impression counterpart:
Mild lumbar spine degenerative disease.
Priority value: 30
Excludes: 8
Suggests: None
If excluded, attempt to insert: None
The selection of phrases based on the definitions above will be illustrated in Examples 2 and 3.

Illustrative Example 2

Figure 3:
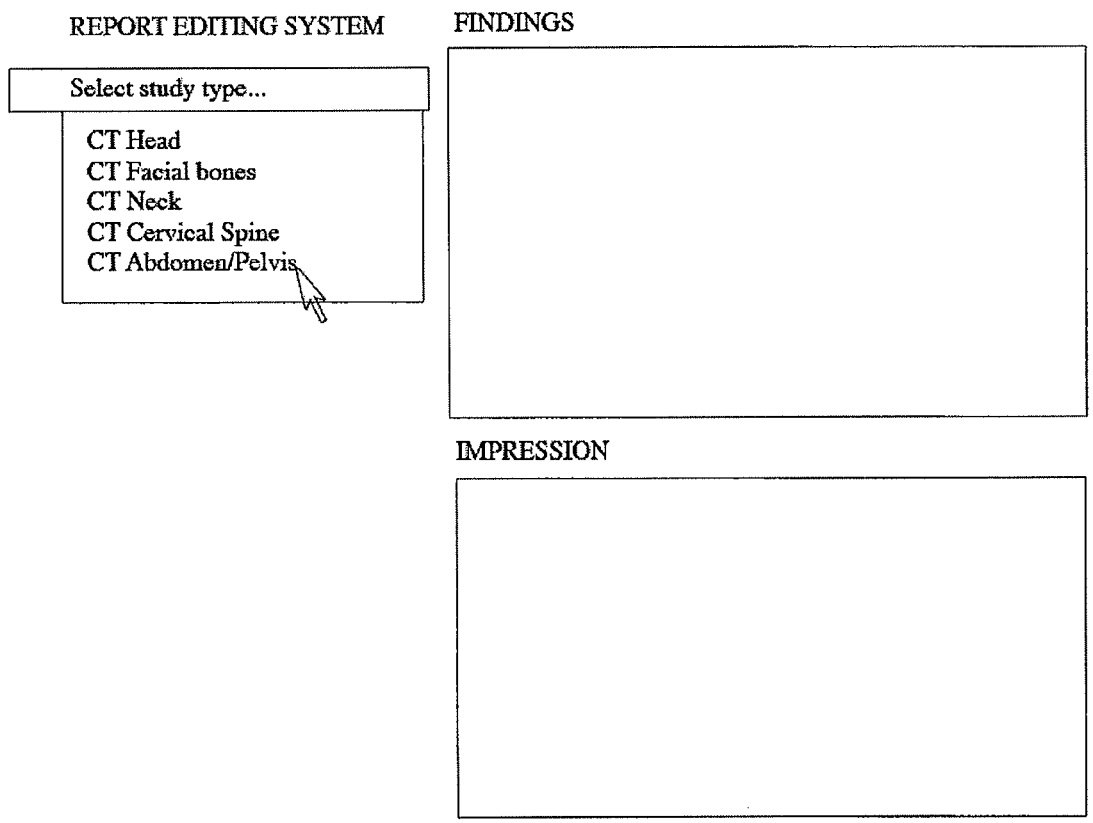

The following is a workflow carried out according to the illustrative embodiment of the present invention and uses the definitions of structures defined in Example 1. First a user selects a type of study from a list of types of studies, for example, CT of the Abdomen and Pelvis, as illustrated in FIG. 3. The report text is populated with a standard normal template for studies of this type. That is, a standard normal report template is employed, which consists of a set of standard phrases inserted into the report together, and used to describe a typical normal study. This standard normal report is definable as such under this system. FIG. 4 illustrates the appearance of the report editing fields after this standard normal template is applied.

Working forward from this standard normal report, the user inserts pathologic or other findings step by step. The phrases in this example have been organized into groups for easy selection by the user. First, the user is presented with a set of pop-up menus referring to the various anatomic regions which are visible or discussible on "CT of the Abdomen and Pelvis." There would be pop-up menus or other GUI elements allowing the user to select pathology for the lung bases, abdomen, pelvis, or bones and soft tissues as illustrated in FIG. 5. If the user were, for example, to click on "Abdomen," then they could select the sub-hierarchy, "Gallbladder," and select the following standard phrase which shows signs of acute cholecystitis. The title of this phrase for easy reference in the menu is "Acute cholecystitis." "Gallstones are noted in the gallbladder, which is mildly distended. There is mild gallbladder wall thickening, and small pericholecystic fluid. Findings are suggestive of acute cholecystitis. Clinical correlation recommended."

This phrase will also be associated with an "impression" counterpart "Gallstones noted in the gallbladder, with mild gallbladder wall thickening, gallbladder distention, and pericholecystic fluid, suggestive of acute cholecystitis."

This phrase is also associated with an exclusionary rule against several of the standard normal expressions. For example, the report can no longer say that there is no free fluid because there is pericholecystic free fluid. The report also cannot say that there is a normal appearance of the abdominal organs and bowel. An exclusionary rule that eliminates the phrase "there is no free fluid or free air" will be applied. There is also an exclusionary rule which prohibits the phrase which states that the abdominal organs and bowel are normal. When the above rule regarding free fluid is excluded by the rule that states the gallbladder/cholecystitis phrase cannot exist in association with this phrase, the "no free fluid or free air" phrase suggests a possible replacement for itself, "There is no free air." This is by means of a relationship between the phrases wherein the phrase "There is no free air" is a standard potential alternate phrase which the system will attempt to insert into the report text when "no free fluid or free air" is excluded. This alternate phrase is not excluded by any other rule, hence it is inserted.

A large set of standard normal statements regarding the abdominal organs may be created, such that when an abnormal finding is inserted into the report, the system will find the first appropriate substitute expression describing a smaller set of normal findings, with the system starting from the "most normal" expression, searching through the list to find the first normal expression which is not excluded by other phrases existing in the report, and finally inserts the first "most normal" normal expression that is not excluded.

In algorithmic terms, when the "normal" expression is excluded from the report, an action is associated with this exclusion, wherein the phrase suggests that the program insert another normal expression in its place. This next expression is checked for exclusions, and if it likewise is excluded, it suggests another normal expression. This continues from one progressively less normal phrase to another until finally one that can be inserted is found. This is inserted into the report.

Each expression also has a "priority" number which determines insertion order into the report. Those items with a higher "priority" number are inserted first. Lower items go later. Higher "priority" numbers are associated with more critical, life-threatening items, or items requiring prompt intervention. The gallbladder phrase regarding cholecystitis will have a high priority number, perhaps seventy out of a possible one hundred. The standard normal expressions have a low priority number, such as one. The report now includes additional phrases that had been selected by the user, and is illustrated in FIG. 6.

Next, the system suggests commonly associated phrases to the user via the knowledge database. These phrases may have be defined by the user at the time the user is organizing their phrases, or could be determined automatically based on prior usage/insertion patterns of phrases. A mature system will involve numerous phrases from each type of source.

Associated with the gallbladder/cholecystis phrase in this example are the following commonly used phrases (a) "No biliary ductal dilatation is seen. No common bile duct stones are seen." and (b) A [#] mm gallstone is also seen in the common bile duct in the pancreatic head, with [MILD/MODERATE/SEVERE] intra and extrahepatic biliary ductal dilatation."

The user selects (b) as s/he also sees a gallstone in the common bile duct with dilated bile ducts. On selecting this phrase, the user types into the [#] blank space a "5," indicating the measurement for the gallstone. The user also selects from among "mild," "moderate," and "severe," to indicate the degree of biliary dilation. The impression counterpart for this phrase is "[#] mm gallstone in the common bile duct with [#] biliary tract dilation." Therefore, the user only enters the measurement and degree of severity information once when they insert the phrase into the report. However, on so doing, at the same time the information is updated in the impression counterpart. The updated report is illustrated in FIG. 7.

The user reviews the list of commonly associated expressions and does not wish to choose anything further. Next, the user may select from the "bones and soft tissues" popup menu, a statement saying "There is mild degenerative disease of the lumbar spine." This expression has a priority value of "5" and its impression counterpart "Mild degenerative disease of the lumbar spine" has a priority value of "5." Therefore these items are less important than the gallbladder statement, but more important than the standard normal report. These statements exclude the statement "The bones and soft tissues are within normal limits." As that phrase is excluded, it attempts to suggest a replacement phrase, "No aggressive appearing bony lesions are seen. The soft tissues are within normal limits." which is not excluded by any phrase currently in the report. Thus, this is inserted. The updated report is shown in FIG. 8.

Alternatively, the user may also prefer to have brief impressions. The user can arbitrarily set a priority value threshold for inclusion of phrase elements in the impression: for example, no more than three findings will be reported, unless such findings have a priority level of fifty or higher. The user would then make sure than any findings which were needed in the impression, if inserted into the report at all, would have to have a priority level of fifty or higher. Since the user has specified that no more than four impression items should be included unless priority values are over fifty, the final report eliminates the fifth item and is illustrated in FIG. 9.

Illustrative Example 3

Figure 10:
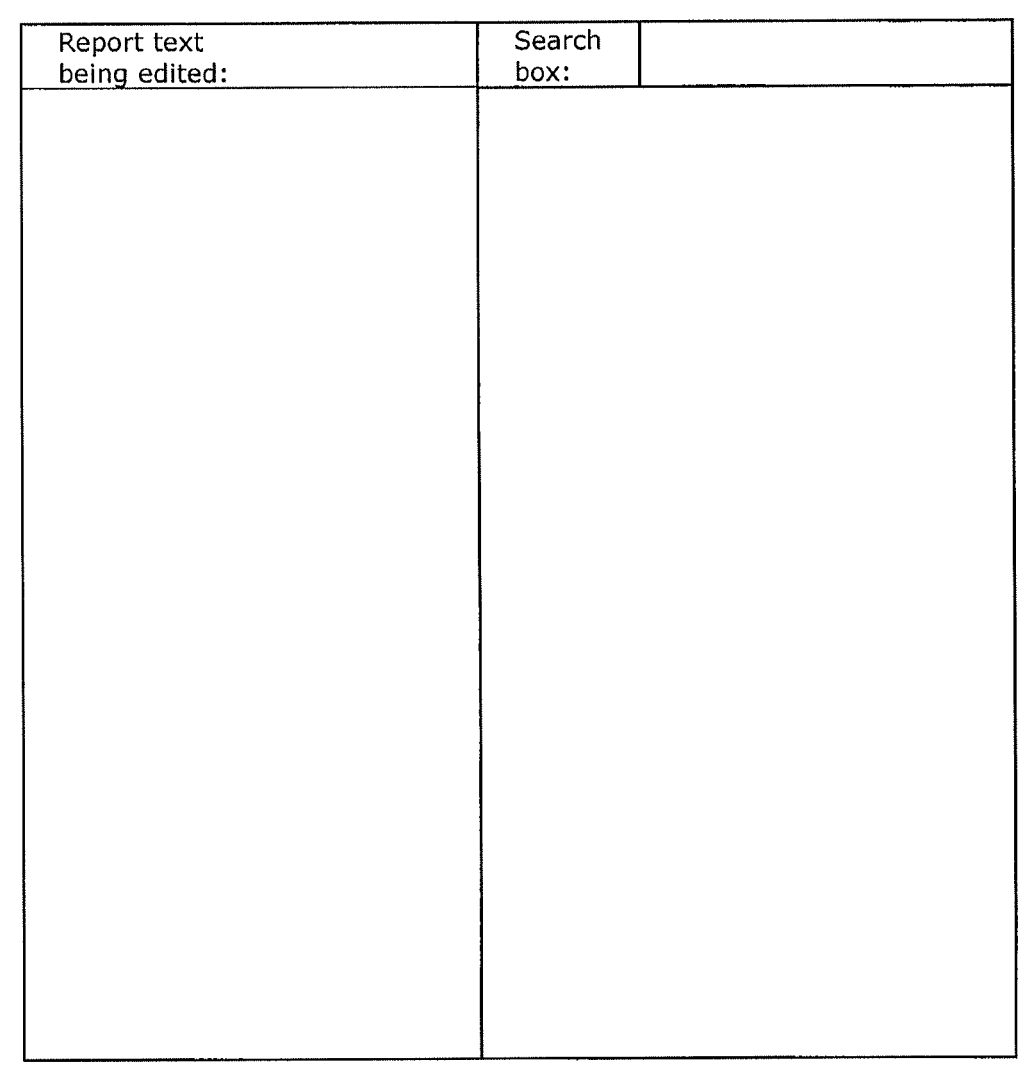

This example shows use of another illustrative embodiment of the invention to edit text fields in a medical imaging study report. In this example, a report on a normal abdominal CT imaging study interpretation is illustrated. First, a user opens a blank reporting screen as shown in FIG. 10. Then the user searches for a normal report template for reporting on a normal abdominal CT imaging study, and types in search terms such as "negative abdominal CT." The system generates several suggested phrases at the server. These phrases have been previously defined and are associated with the search terms. The suggested phrases are then displayed for the user to review, as shown in FIG. 11. The user selected the first suggested phrase, which is entered into the report edit field as shown in FIG. 12. In doing so, several updated suggestions are made based on prior usage patterns of the system of this user, other users in the system and words in the report text. In this example as illustrated in FIG. 13, the patient is a 70 year-old male, and his age and gender information is also inputted into the system, which is then used to suggest other phrases and expressions, such as probable osteopenia, which are commonly selected when users edit reports for patients of that age and gender group. The user may save the entire template or a portion of the template to the general knowledge database for future use in cases with similar findings.

Having the basic report framework in place, the user wishes to report about an abnormality. In this example, a right renal mass about 5 cm in size of intermediate density is obstructing the right kidney (right sided hydronephrosis). The user decides to search for phrases about renal masses in the search box of the report interface as shown in FIG. 14. At the time of the imaging interpretation, the user is not sure what the mass is, but thinks the first expression in FIG. 14 is a useful framework to start with, and thus selects that expression. The user also enters values into the sections where the size of the mass and a choice between "left" and "right" for a parameter are given. The orientation data (i.e. left or right) and size data only need to be inputted in one place and are propagated throughout the text as shown in FIG. 15. This allows a user to save time from entering repetitive information and reduces reporting error. Upon adding the renal mass phrase, the system applies exclusion rules to the phrases to detect inconsistencies and conflicts. The expressions in the initial normal report inserted by the user that are in conflict with the renal mass finding are flagged, such as in italics and in red, to alert the user of the potential inconsistency. The user can click on the italicized and red expression to delete, edit, or select commonly substituted expression, as shown in FIG. 16. FIG. 17 shows the substituted phrases that are suggested by the system upon a user clicking on the first red-italicized expression. A user may update the report as shown in FIG. 18.

FIG. 19 shows how a user may also insert freestyle text in sub-text fields to the defined expressions to report details that are not included in the common expressions from the database. This allows a user to deviate from the standard defined expressions to fully customize a report. In this example, the user added "or hemorrhagic angiomyelolipoma" in the impression. Upon adding this text, the system identifies "angiomyelolipoma" as an uncommon term that may be of value in the suggestion of additional phrases. Additional phrases which include the term angliomyelolipoma are then suggested to the user via the interface, as shown in FIG. 20. The user chooses to insert an additional phrase regarding angiomyelolipomas into the report as shown in FIG. 21, and finalizes the report.

FIG. 22 shows a screen shot of the system interface according to an illustrative embodiment of the invention.

The invention includes the methods as described herein, a computer readable medium programmed to carry out the methods and a computer system configured to carry out the methods. The computer system includes a machine readable storage medium containing executable code; an apparatus having one or more processors; memory coupled to a processor; a machine-readable medium having machine-readable program code; an input device and an output device connected to the processor(s) to produce the reports or other material. While the invention is described by illustrative embodiments, additional advantages and modifications will occur to those skilled in the art. Therefore, the invention in its broader aspects is not limited to specific details shown and described herein.

Modifications, for example, to the type of reports and particular features of the software, may be made without departing from the spirit and scope of the invention. Accordingly, it is intended that the invention not be limited to the specific illustrative embodiments, but be interpreted within the full spirit and scope of the described embodiments and appended claims and their equivalents.

The invention claimed is:

1. A computer-based method for generating a medical imaging study report comprising the steps of:
storing a medical imaging report generation database in a computer readable medium, the medical imaging report generation database containing one or more of the following: (a) phrases relevant to a plurality of image study types interpreted in a medical imaging study, (b) relationships between those phrases, and (c) templates consisting of a set of such phrases, and/or (d) the full text of previously authored reports from within and/or outside of the system, from which phrase suggestions can be derived;
storing executable computer code in a computer processor linked to the computer readable medium;
generating, by executing the computer code using the computer processor, a medical imaging study report for display on a computer display device, using the stored report generation database, wherein the medical imaging study report contains an architecture accommodating one or more text fields;
generating by executing the computer code using the computer processor, a plurality of study types for display to the user via a user-output device;
upon the user selecting a study type via a user-input device, providing by executing the computer code using the computer processor, one or more suggested first phrases of potential interest from the report generation database based on the selected study type, and/or by a template selected by the user, to the user via the use-output device;
upon the user selecting one or more first phrases via the user-input device, providing via the user-output device by executing the computer code using the computer processor, one or more suggested related phrases of potential interest from the report generation database based on the selected first phrases;
upon the user selecting one or more related phrases via the user-input device, and/or the user inputting any other desired arbitrary text into the report, applying by executing the computer code using the computer processor, one or more inclusion rules based on patterns of use, to the one or more selected first phrases, and/or by applying pattern-matching rules to identify potentially useful text from other reports stored in the previously authored radiology report database, and presenting the one or more suggested phrases to the user via a user-output device;
applying via the user-output device, by executing the computer code using the computer processor, one or more exclusion rules based on patterns of usage to the one or more first phrases and/or the one or more related phrases and/or the report in progress to identify one or more excluded phrases to be excluded from the report;
and generating a report resulting from these processes to be sent to the report output device.

2. The method of claim 1 further comprising:
updating the exclusion rules and inclusion rules based on at least a portion of the generated report, and inclusion and exclusion selection decisions made by the user.

3. The method of claim 2 further comprising implementing the method over a network, wherein updating the exclusion rules and inclusion rules is based on at least a portion of one or more reports generated by one or more users.

4. The method of claim 1 further comprising: providing medical imaging data associated with one or more medical imaging studies corresponding to one or more anatomical regions to be reviewed and to be interpreted in a medical imaging study; and generating by executing the computer code using the computer processor, one or more suggested study types based on the medical imaging data.

5. The method of claim 1 wherein at least a portion of the one or more text fields are populated by one or more templates, each template containing a set of phrases relevant to the study type selected.

6. The method of claim 1 further including the steps of: assigning a priority value to one or more of the phrases; and ordering by executing the computer code using the computer processor the phrases in the report according to the priority values.

7. The method of claim 1, wherein one or more text fields further include one or more sub-fields for user-input text, where the user-input text is optionally propagated in the text fields of related phrases in the report.

8. The method of claim 1 further comprising: saving to the medical imaging report database data representing the frequency of use of modified phrases; comparing the frequency of use of the modified phrases with the frequency of use of corresponding unmodified phrases; and presenting any suggested phrases as modified phrases in place of any corresponding unmodified phrases, with a lower frequency of use.

9. The method of claim 1 further comprising:
saving to the medical imaging report database data representing the frequency of use of modified templates;
comparing the frequency of use of the modified templates with the frequency of use of corresponding unmodified templates; and presenting any suggested templates as modified templates in place of any corresponding unmodified templates, with a lower frequency of use.

10. A medical imaging study report generation system comprising:
one or more input devices to input study type selection, phrase selection, and text;
one or more processors to process the study type selection, the phrase selections, the text, and one or more rule-based concepts;
one or more memory systems functionally coupled to the processors; and
an output device functionally connected to the processors;
wherein the system is configured to carry out the report generation steps of claim 1.

11. A computer-based method for generating a medical imaging study report comprising the steps of:
storing a medical imaging report generation database in a computer readable medium, the medical imaging report generation database containing at least one of the following: (a) phrases associated with a plurality of image study types interpreted in a medical imaging study and inclusion and exclusion rules, and/or (b) report templates consisting of aggregations of such phrases, and/or (c) data regarding prior patterns of usage of such phrases in previous instances of use of the system, and/or (d) a database of full report texts which can be drawn upon to identify additional phrase suggestions;
executing computer code using a computer processor linked to the computer readable medium;
generating, by executing the computer code using the computer processor, a medical imaging study report on display on a computer display device, using the stored report generation database, wherein the medical imaging study report contains an architecture accommodating one or more text fields;

presenting a plurality of study types for display to the user via a user-output device by executing the computer code using the computer processor;

upon the user selecting a study type via a user-input device, providing to the user via the user-output device by executing the computer code using the computer processor, a report template having a plurality of phrases based on the selected study type;

presenting one or more phrases related to the template phrases via the user-output device;

upon the user selecting one or more related phrases, applying by executing the computer code using the computer processor, one or more inclusion rules based on patterns of usage to the template phrases and the selected related phrases; upon the user selecting one or more related phrases, applying to the template phrases and the selected related phrases by executing the computer code using the computer processor one or more exclusion rules based on patterns of usage to the phrases, thereby identifying one or more phrases to be excluded from the medical imaging report;

generating a medical imaging report containing the selected phrases in the text fields and the study type via a report output device; and updating the database by saving back into the database at least a portion of, or all of, the text in the generated report, and inclusion and exclusion selection decisions made by the user.

12. The method of claim 11 wherein one or more template phrases and one or more related phrases are associated with priority values, the method further comprising:

presenting in the medical report to the user via the user-output device the one or more prioritized related phrases and prioritized template phrases ordered according to their associated priority values.

13. The method of claim 11 further comprising:
defining a set of templates associated with a particular user.

14. The method of claim 11 further comprising:
presenting phrases based on patterns of use of the phrases.

15. The method of claim 11 further comprising:
presenting phrases based on their frequency of use in like reports, and identifying new phrases based on use in prior reports.

16. The method of claim 1 or 11 further comprising:
saving to the medical imaging report database data representing the frequency of use of modified phrases;
comparing the frequency of use of the modified phrases with the frequency of use of corresponding unmodified phrases; and
presenting any suggested phrases as modified phrases in place of any corresponding unmodified phrases, with a lower frequency of use.

17. The method of claim 1 or 11 further comprising:
saving to the medical imaging report database data representing the frequency of use of modified templates;
comparing the frequency of use of the modified templates with the frequency of use of corresponding unmodified templates; and
presenting any suggested templates as modified templates in place of any corresponding unmodified templates, with a lower frequency of use.

18. The method of claim 1 or 11 further comprising:
saving to the medical imaging report database all or part of the text in the report generated by the user, including any arbitrary new text generated uniquely by and inputted into the system by the user.

19. The method of claim 11 further comprising upon any phrases or text being entered into the system by the user, using pattern-matching methods to identify phrases from previously defined phrases within the system, as well as text contained within the database of previously authored radiology reports, and suggesting additional possible phrases which the user may wish to incorporate into the report.

20. The method according to claim 19 further comprising sorting the suggested additional phrased based on or more of the following factors: the frequency with which other users have selected the text suggestions in question; the frequency with which other users have selected other text suggestions authored by the same author as a given text suggestion; the frequency with which the current user of the system has selected other text expressions authored by the author of the text suggestion in question; the number of words in the current text edit field being worked on by the current user of the system which also appears in the text suggestion in question, with this last factor amplified by the infrequency of the words in question; medical imaging study meta-data.

21. The method of claim 1 wherein at least one exclusion rule, upon a determination that two incompatible report terms are found in the repot, the incompatible terms are identified for the user.

22. The method of claim 1 further comprising maintaining a user-specific knowledge database for at least one user.

23. The method of claim 1 further comprising accepting for each of at least two findings a priority, and selecting a limited number of findings for inclusion in a report based upon the relative priority of the one findings.

* * * * *